United States Patent
Mackenzie et al.

(10) Patent No.: US 10,692,395 B2
(45) Date of Patent: Jun. 23, 2020

(54) AUTOMATED SURGEON PERFORMANCE EVALUATION

(71) Applicant: University of Maryland, Baltimore, Baltimore, MD (US)

(72) Inventors: Colin F. Mackenzie, Pasadena, MD (US); Shiming Yang, Halethorpe, MD (US); Fu-Ming Hu, Ellicott City, MD (US); Evan Garofalo, Phoenix, AZ (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 305 days.

(21) Appl. No.: 15/753,337

(22) PCT Filed: Aug. 17, 2016

(86) PCT No.: PCT/US2016/047292
§ 371 (c)(1),
(2) Date: Feb. 19, 2018

(87) PCT Pub. No.: WO2017/031175
PCT Pub. Date: Feb. 23, 2017

(65) Prior Publication Data
US 2018/0247560 A1    Aug. 30, 2018

Related U.S. Application Data

(60) Provisional application No. 62/205,955, filed on Aug. 17, 2015.

(51) Int. Cl.
*G09B 19/00* (2006.01)
*G09B 23/28* (2006.01)
(Continued)

(52) U.S. Cl.
CPC ............ *G09B 19/003* (2013.01); *A61B 16/00* (2013.01); *A61B 17/00* (2013.01); *A61B 42/10* (2016.02);
(Continued)

(58) Field of Classification Search
CPC ........ G09B 19/00; G09B 19/003; G09B 5/00; G09B 5/02; G09B 5/04; G09B 23/28;
(Continued)

(56) References Cited

U.S. PATENT DOCUMENTS 6,069,691 A    5/2000 Rosow et al.
2001/0031920 A1* 10/2001 Kaufman ............... A61B 5/055
600/431
(Continued)

FOREIGN PATENT DOCUMENTS

KR    101355963 B1    1/2014
KR    101554429 B1    9/2015

OTHER PUBLICATIONS

Ahmidi, N., et al., Automated objective surgical skill assessment in the operating room from unstructured tool motion in septoplasty, Int J Comput Assist Radio! Surg, 2015, pp. 981-991, vol. 10, Issue 6.
(Continued)

*Primary Examiner* — Timothy A Musselman
(74) *Attorney, Agent, or Firm* — Beusse Wolter Sanks & Maire; Eugene J. Molinelli

(57) ABSTRACT

Techniques for automated surgeon performance evaluation include dressing an operator with colored surgical gloves. A first glove for a dominant hand has a first color and a second glove for the other hand has a different second color. Video data that views the operator's hands is captured during a surgical procedure on a subject. For each of multiple frames of the video data, a minimum rectangle of pixels, called a first rectangle, which encloses pixels having the first color, (Continued)

is determined automatically on a processor. A first time series for a representative property of the first rectangle at the multiple frames, and a first measure of entropy based on the first time series, are also automatically determined on a processor. A metric of operator performance based at least in part on the first measure of entropy is stored, e.g., for subsequent display.

17 Claims, 11 Drawing Sheets

(51) Int. Cl.
| | |
|---|---|
| G09B 5/04 | (2006.01) |
| A61B 42/10 | (2016.01) |
| A61B 90/00 | (2016.01) |
| A61B 90/92 | (2016.01) |
| G06T 7/246 | (2017.01) |
| A61B 16/00 | (2006.01) |
| A61B 17/00 | (2006.01) |
| G06K 9/00 | (2006.01) |
| G06K 9/46 | (2006.01) |
| G09B 5/02 | (2006.01) |

(52) U.S. Cl.
CPC .......... *A61B 90/361* (2016.02); *A61B 90/92* (2016.02); *G06K 9/00355* (2013.01); *G06K 9/00744* (2013.01); *G06K 9/4642* (2013.01); *G06K 9/4652* (2013.01); *G06T 7/248* (2017.01); *G09B 5/02* (2013.01); *G09B 5/04* (2013.01); *G09B 23/28* (2013.01); *A61B 2560/0223* (2013.01); *G06T 2207/10016* (2013.01); *G06T 2207/10024* (2013.01); *G06T 2207/20021* (2013.01); *G06T 2207/30196* (2013.01)

(58) Field of Classification Search
CPC .. G09B 23/282; G09B 23/285; G09B 23/286; A61B 42/10; A61B 16/00; A61B 17/00; A61B 2560/0223; G06T 7/248; G06T 2207/10016; G06T 2207/10024; G06T 2207/20021; G06T 2207/30196
See application file for complete search history.

(56) References Cited

U.S. PATENT DOCUMENTS

| | | |
|---|---|---|
| 2005/0214727 A1 | 9/2005 | Stoianovici et al. |
| 2014/0220527 A1 | 8/2014 | Li et al. |

OTHER PUBLICATIONS

Cao, C.L. and Milgram, P., Direction and location are not sufficient for navigating in nonrigid environments: an empirical study in augmented reality, Presence: Teleop Virt, 2006, pp. 584-602, vol. 16, Issue 6.
D'Angelo, A.L., et al., Idle time: an underdeveloped performance metric for assessing surgical skill, Am J Surg, 2015, pp. 645-651, vol. 209, Issue 4.
Datta, V., et al., The use of electromagnetic motion tracking analysis to objectively measure open surgical skill in the laboratory-based model, J Am Coll Surg, 2001, pp. 479-485, vol. 193, Issue 5.
Datta, V., et al., The surgical efficiency score: a feasible, reliable, and valid method of skills assessment, Am J Surg, 2006, pp. 372-378, vol. 192, Issue 3.
Digioia, A.M., et al. HipNav: Pre-operative planning and intra-operative navigational guidance for acetabular implant placement in total hip replacement surgery, Proc Comp Assis Ortho Surg Symposium (CAOS), Bern, 1995.
Dosis, A., R., et al. Synchronized video and motion analysis for the assessment of procedures in the operating theater, Arch Surg, 2005a, pp. 293-299, vol. 140, Issue 3.
Gambadauro, P., and A. Margos, Surgical videos for accident analysis, performance improvement, and complication prevention: time for a surgical black box?, Surg Innov, 2012, pp. 76-80, vol. 19, Issue 1.
Kranzfelder, M., et al., Shock/Sepsis/Trauma/Critical Care: Real-time instrument detection in minimally invasive surgery using radiofrequency identification technology, J Surg Res, 2013, pp. 704-710, vol. 185, Issue 2.
Mackenzie, C.F., et al., Using an Individual Procedure Score before and after the advanced surgical skills exposure for trauma course training to benchmark a hemorrhage-control performance metric, J Surg Educ Jul. 23, 2015, pii: S1931-7204(15)00161-0. doi: 10.1016/j.jsurg.2015.06.009. [Epub ahead of print].
Martin, J.A., et al., Objective structured assessment of technical skill (OSATS) for surgical residents, Br J Surg, 1997, pp. 273-278, vol. 84, Issue 2.
Moorthy, K., et al., Objective assessment of technical skills in surgery, BrMed J, 2003, pp. (1032-1037), vol. 327, Issue 7422.
Overby, D. and R. Watson, Hand motion patterns of fundamentals of laparoscopic surgery certified and noncertified surgeons, Am J Surg, 2014, pp. 226-230, vol. 207, Issue 2.
Reiley, C.E. and G.D. Hager, Task versus subtask surgical skill evaluation of robotic minimally invasive surgery, Proceedings of the 12th International Conference on Medical Image Computing and Computer-Assisted Intervention (MICCAI), Part I. Springer: Berlin, 2009, pp. 435-442.
Shackelford, S., et al., Development and validation of traumatic surgical skills metrics: Preliminary assessment of performance after training, J Trauma Acute Care Surg, 2015, pp. 105-110, vol. 79, Issue 1.
Stergiou, N., et al., Optimal movement variability: a new theoretical perspective for neurological physical therapy, J Neurol Phy Ther, 2006, pp. 120-129, vol. 30.
Taylor, J.A. and R.B. Ivry, Cerebellar and prefrontal cortex contributions to adaptation, strategies, and reinforcement learning, Prog Brain Res, 2014, pp. 217-253, vol. 210.
Uemura, M., et al., Analysis of hand motion differentiates expert and novice surgeons, J Surg Res, 2014, pp. 8-13, vol. 188, Issue 1.
Watson, R.A., Computer-aided feedback of surgical knot tying using optical tracking, J Surg Educ, 2012, pp. 306-310, vol. 69, Issue 3.
Watson, R.A., Use of machine learning algorithm to classify expertise: analysis of hand motion patterns during a simulated surgical task, Acad Med, 2014, pp. 1163-1167, vol. 89, Issue 8.
Zappella, L., et al., Surgical gesture classification from video and kinematic data, Med Image Analysis, 2013, pp. 732-745, vol. 17, Issue 7.
Gray, R., et al., High-fidelity, low-cost, automated method to assess laparoscopic skills objectively, J Surg Educ, 2012, pp. 335-339, vol. 69, Issue 3.
ISA/US "International Search Report and Written Opinion for the corresponding PCT application PCT/US2016/047292", dated Oct. 27, 2016, pp. 1-7.

\* cited by examiner

FIRST COLORED GLOVE 230a
SECOND COLORED GLOVE 230b
SUBJECT 290

MINIMUM RECTANGLE 234a
MINIMUM RECTANGLE 234b
PIXELS OF FIRST COLOR 232a
PIXELS OF SECOND COLOR 232b
FIRST RECTANGLE CENTER POINT 236a
SECOND RECTANGLE CENTER POINT 236b

AUTOMATED SURGEON PERFORMANCE EVALUATION

CROSS-REFERENCE TO RELATED APPLICATIONS

This application is a 371 national stage application of PCT Application No. PCT/US16/47292, filed Aug. 17, 2016, and claims benefit of Provisional Appln. 62/205,955, filed Aug. 17, 2015, the entire contents of which are hereby incorporated by reference as if fully set forth herein, under 35 U.S.C. § 119(e).

STATEMENT OF GOVERNMENTAL INTEREST

This invention was made with government support under W81XWH-13-2-0028 awarded by the U.S. Army Medical Research and Material Command. The government has certain rights in the invention.

BACKGROUND

Surgical residents' technical skill is typically evaluated from observations by experienced mentors during training; however this process is time consuming, labor intensive and subjective, and may include evaluator biases. Efforts have been made to standardize surgical trainee evaluations and eliminate bias. The most frequent performance evaluation currently used is the objective structured assessment of technical skills (OSATS).

The correlation between hand motion and surgical skill has been extensively documented over the past decade. Metrics such as smoothness of movement, velocity and acceleration, path length of the hand, entropy levels, idle time, and the comparative usage of dominant and non-dominant hands have been shown to be significantly related to surgical experience (Ahmidi 2015; D'Angelo 2015; Datta 2001, 2006; Dosis 2005; Gray 2012; Moorthy 2003; Overby 2014; Uemura 2014; Watson 2012, 2014). However, the majority of previous studies relied on synthetic models or non-surgical tasks to simplify the hand motion analysis (D'Angelo 2015; Datta 2001, 2006; Gray 2012; Moorthy 2003; Overby 2014; Uemura 2014; Watson 2012, 2014). Multiple reports have described tools to measure and track hand motion during rigid endoscopy (e.g. laparoscopy, arthroscopy) (Ahmidi 2015; Dosis 2005a, 2005b) and during use of robotic surgery devices (Reiley 2009). Tracking hand motions while using flexible endoscopes is more difficult, since operator hand movements do not translate directly into movement of the distal end of the flexible endoscope, especially in mobile environments such as the colon (Cao 2006). Hand movement tracking data is useful to assist intraoperative navigation to position acetabular implants (Digioia 1995) and for quantifying the benefits of training (Gambadauro 2012). Manual dexterity parameters, including time to perform, motion economy, hand & tool movement, and instrument path length, among others, are related to levels of surgeon experience (Ahmidi 2015; D'Angelo 2015; Datta 2001, 2006; Gray 2012).

SUMMARY

While suitable for many purposes, it is here noted that several deficiencies abide in the prior approaches to surgeon performance evaluation. Few studies examine hand motion with open surgical procedures, because tracking surgeon hand motion in this setting is more complex (Datta 2001). Many studies require the placement of one or more sensors on the hands of the surgeon being evaluated, which can interfere with the movement of even the most experienced surgeons. Thus such sensors are typically not used during actual surgical procedures. Furthermore, open surgical procedures vary widely, requiring specialized sensor placement and assessment methods that allow for freedom of hand and instrument movement.

It is here recognized that, ideally, these automated, objective hand motion methods should be hand-sensor-free to avoid interference with hand motion and surgical performance. Techniques are provided for hand-sensor-free, automated detection of hand motion suitable for surgeon performance evaluation. Because the techniques can be used with persons who are not surgeons, such as trainees, interns, residents, paramedics, anatomists, and users of manual tools, the person being evaluated herein is called an operator. The subject being operated upon by the procedure is called a subject and can include both human and animal patients, both alive and no longer alive, such as cadavers that were once alive.

In a first set of embodiments, a method includes dressing an operator with colored surgical gloves for which a dominant hand of the operator wears a first surgical glove having a first color on at least a portion of the first glove and a non-dominant hand of the operator wears a second surgical glove having a different second color on at least a portion of the second glove. The method further includes, after dressing the operator, capturing video data that views the operator's hands during a surgical procedure on a subject. Still further, the method includes, for each of multiple frames of the video data, automatically determining, on a processor, a minimum rectangle of pixels (called a first rectangle) that encloses pixels having the first color. Even further, the method includes determining automatically on a processor a first time series for a representative property of the first rectangle at the multiple frames. Even yet further, the method includes determining automatically on a processor a first value for a first measure of entropy based on the first time series; and storing, on a computer-readable medium, a metric of operator performance based at least in part on the first value for the first measure of entropy. In some embodiments, the metric is presented on a display device, such as a graphical user interface that lists the metric for one or more operators.

In some of the embodiments of the first set, the first color and the second color are each different from a color of any item that is not a surgical glove of the operator in the video data that views the operator's hands during the surgical procedure.

In some embodiments of the first set, the method also includes providing a calibration curve that relates values of the first measure of entropy to values of independently assessed experience of an operator for a plurality of different operators during a training session; the metric is based on the calibration curve and the first value for the first measure of entropy value.

In some embodiments of the first set, the plurality of frames are confined to a time interval associated with a stage of the procedure, such as one or more of a tool arranging stage, a cutting stage, a spreading stage, a manipulation stage, or a suturing stage.

In some embodiments of the first set, the representative property of the first rectangle is a center point of the first rectangle. In some of these embodiments, the time series of the representative property is a time series of a set of one or more values, wherein the one or more values indicate one or more of position, speed, direction, acceleration magnitude or direction change of the center point.

In some embodiments of the first set, the method also includes, for each of the frames of the video data, automatically determining, on a processor, a minimum rectangle of pixels, called a second rectangle, that encloses pixels having the second color. In these embodiments, the method also includes determining automatically on a processor a second time series of a representative property of the second rectangle at the plurality of frames, and determining automatically on a processor a second value for a second measure of entropy based on the second time series. In these embodiments; the metric of operator performance is based at least in part on the second value for the second measure of entropy. In some of these embodiments, the second measure of entropy is joint entropy of the first time series and the second time series.

In other sets of embodiments, an apparatus or system or non-transitory computer-readable medium carries out one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus are described for automated, objective, hand-sensor-free evaluation of performance of an operator during a surgical procedure. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of one type of procedure on cadavers. However, the invention is not limited to this context. In other embodiments any surgery on any living or formerly living human or animal subject can be evaluated for any purpose, including training, certification, recertification, promotion, monitoring of individuals or groups of operators.

1. OVERVIEW

Computer-based, hand-sensor-free metrics for surgeon hand-motion entropy presented here are found to powerfully discriminate expertise during surgical procedures. Metrics improve with training, deteriorate over time, and are congruent with a validated performance-based individual procedure score. These new hand-motion metrics can provide objective, less labor-intensive surgical performance evaluations and are a step to automated surgical technical skills assessment.

Figure 1:
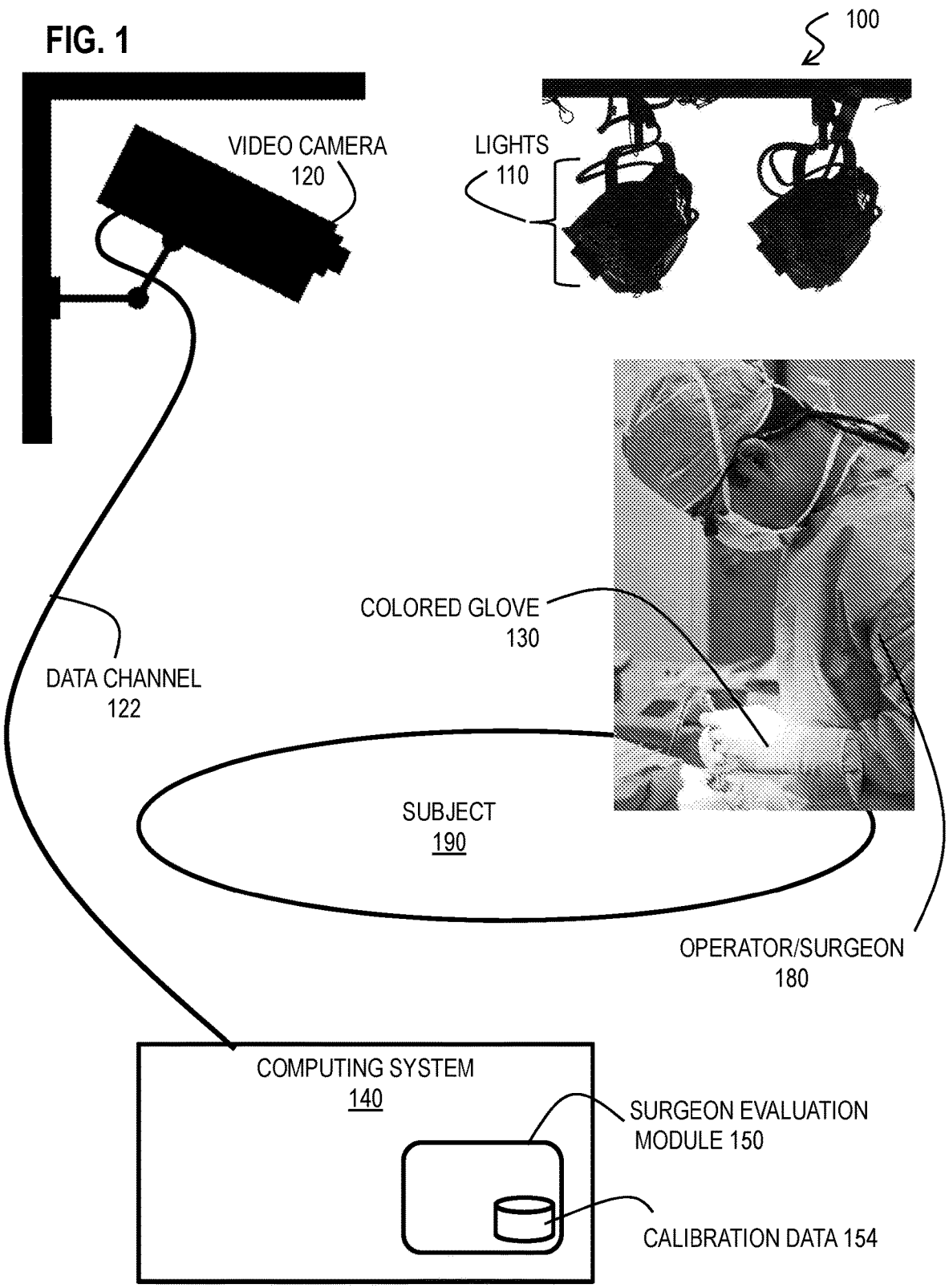
FIG. 1 is a block diagram that illustrates an example system for automatically evaluating operator performance during a surgical procedure, according to an embodiment.

FIG. 1 is a block diagram that illustrates an example system 100 for automatically evaluating operator performance during a surgical procedure, according to an embodiment. Although a subject 190 and operator or surgeon 180 are shown for purposes of illustration, the system does not include the subject 190 or operator or surgeon 180. The illustrated system 100 includes one or more lights 110 that emit light containing wavelengths associated with at least a first color, and in some embodiments, a similar amount (flux) of light of wavelengths associated with a different second color. In some embodiments, the lights 110 are the same as white lights ordinarily found in a surgical operating room. The system also includes a video camera 120. The system also includes a computing system 140, such as the computing system described below with reference to FIG. 6 or a chip set described below with reference to FIG. 7. The computing system 140 is configured with a surgeon evaluation module 150, such as software that implements one or more steps of the flow diagram described below with reference to FIG. 5. In various embodiments, the surgeon evaluation module 150 generates or uses calibration data 154 stored on a computer-readable medium. The system 100 includes at least one colored glove having at least a portion of the glove colored with the first color that can be discriminated from other objects in a field of view of the video camera 120. In some embodiments, the system includes a second colored glove of a different second color having at least a portion of the glove colored with the second color that also can be discriminated from other objects in a field of view of the video camera 120. The video data collected by video camera 120 is communicated to the computer system 140 with the surgeon evaluation module 150 via data channel 122, such as a wired or wireless communication channel.

During operation of the system, the at least one colored glove is donned by the operator 180 to be evaluated, and the lights 110 and video camera 120 are directed to illuminate and record, respectively, the at least one colored glove for an interval of time while the operator 180 performs a surgical procedure on the subject 190. In some embodiments, the first glove with the first color is donned on a dominant hand of the operator, e.g., on a right hand of a right-handed operator or on a left hand of a left-handed operator. In some embodiments, the second glove with the second color is donned on the other hand, called the non-dominant hand, of the operator 180.

Although processes, equipment, and data structures are depicted in FIG. 1 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Figure 2A:
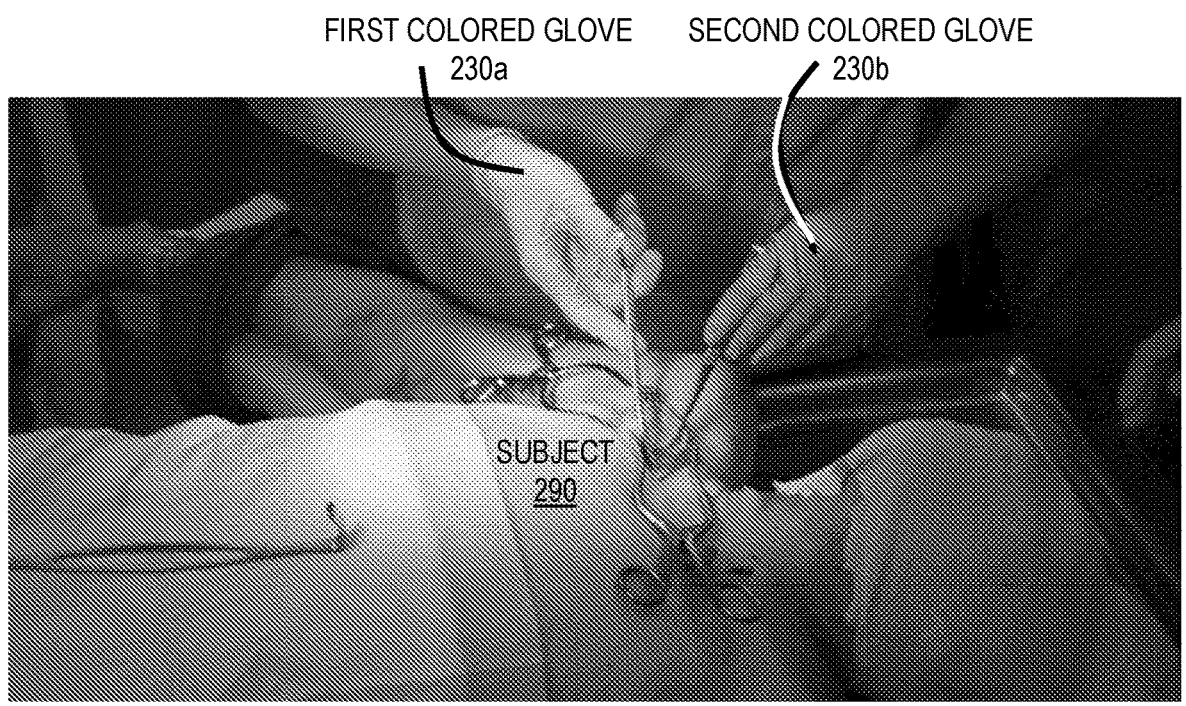
FIG. 2A is an image that illustrates an example frame of video data that views differently colored gloves on the hands of an operator during a surgical procedure, according to an embodiment.

FIG. 2A is an image that illustrates an example frame of video data that views differently colored gloves on the hands of an operator during a surgical procedure, according to an embodiment. Evident in the frame is the subject 290 and a first colored glove 230a of the first color and a second colored glove 230b of the different second color.

Figure 2B:
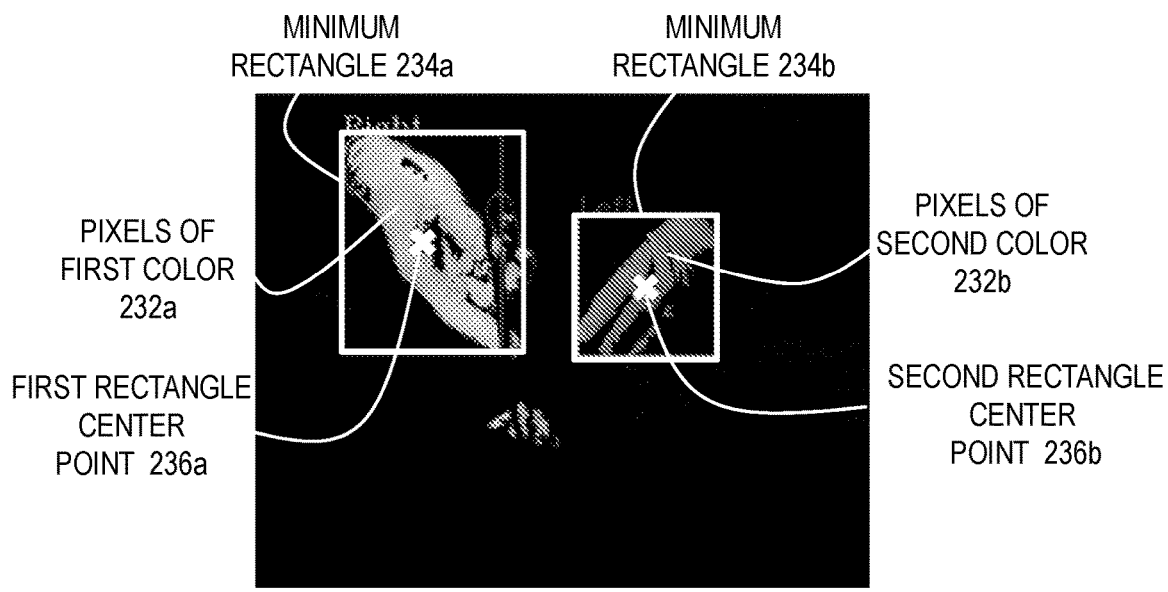
FIG. 2B is an image that illustrates an example bitmap of pixels containing the two colors of the gloves and the associated minimum rectangle that encompasses each color, according to an embodiment.

FIG. 2B is an image that illustrates an example bitmap of pixels containing the two colors of the gloves and the associated minimum rectangle that encompasses each color, according to an embodiment. The image is made by cropping the frame of FIG. 2A to an area of interest, and turning black each pixel that is not within a range of digital values corresponding to a first color or second color. Pixels within a range of digital values that correspond to the first color are colored with the first color to produce called pixels of first color 232a; and pixels within a range of digital values that correspond to the second color are colored with the second color to produce pixels of second color 232a. Because of shadows and shading each of the first color or the second color is represented by a range of digital values, e.g., by the same ratio of base colors, such as red to green to blue in an RGB system (or other three color base, such as magenta, cyan, yellow) but at different intensity levels (e.g., intensity is usually in a range from 0 to 255 for each base color). Image processing software is available to determine that a pixel is within a range of digital values that correspond to a first color with shading. A minimum rectangle that encloses the pixels of each color is called a minimum rectangle. The minimum rectangle 234a encloses pixels of the first color and the minimum rectangle 234b encloses pixels of the second color.

Figure 2C:
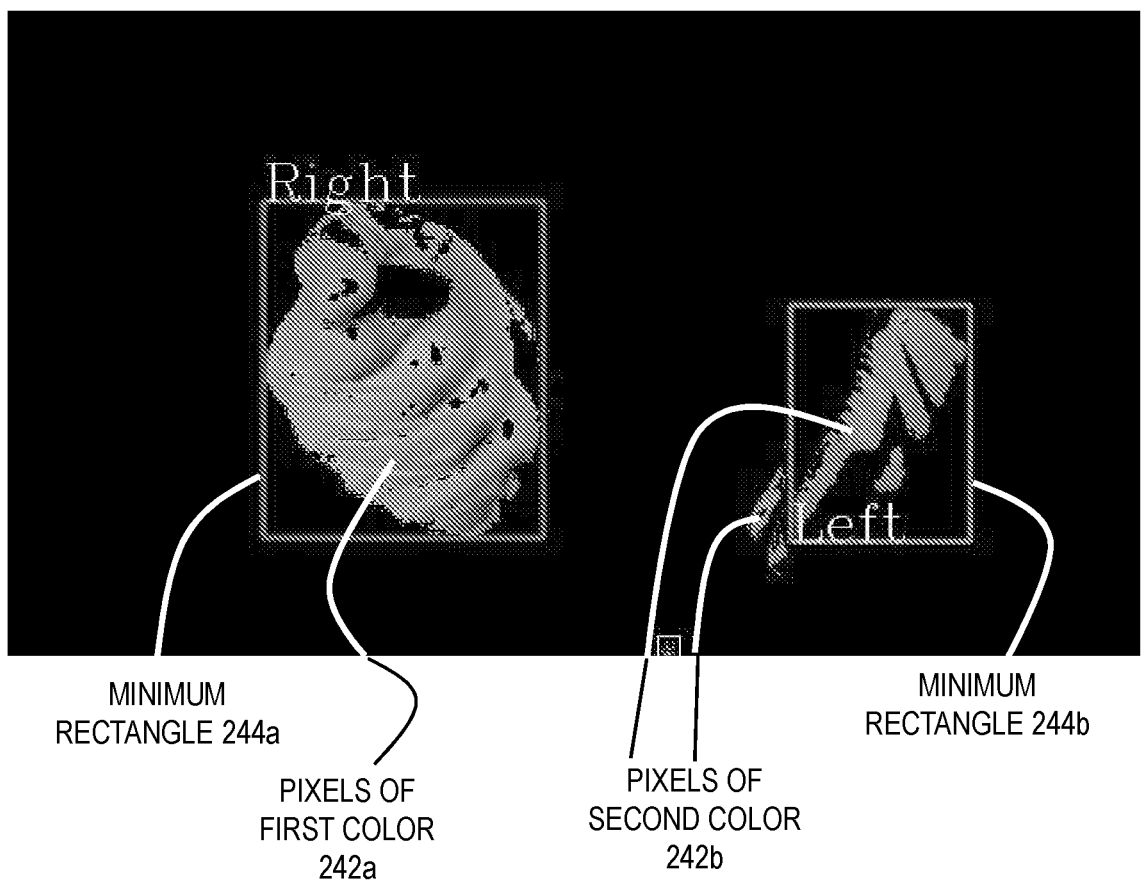
FIG. 2C is an image that illustrates an example bitmap of pixels containing the two colors of the gloves and the associated minimum rectangle that encompasses the largest connected area of each color used as a minimum bounding rectangle, according to an embodiment.

FIG. 2C is an image that illustrates an example bitmap of pixels containing the two colors of the gloves and the associated minimum rectangle that encompasses the largest connected area of each color used as a minimum bounding rectangle, according to an embodiment. As in FIG. 2B, this image is made by cropping a frame to an area of interest, and turning black each pixel that is not within a range of digital values corresponding to a first color or second color. Pixels within a range of digital values that correspond to the first color are colored with the first color to produce colored pixels of first color 242a; pixels within a range of digital values that correspond to the second color are colored with the second color to produce pixels of second color 242b. Because of shadows and shading, each of the first color or the second color is represented by a range of digital values. Also, due to shadows or noise or clutter, several disconnected sets of pixels are formed. Thus several minimum connected rectangles can be formed that each encloses a connected area of pixels of the first color or second color. See for example several connected areas of pixels of the second color 242b. In some embodiments a minimum rectangle is defined as the largest of the minimum connected rectangles. The minimum rectangle 244a encloses the largest connected area of pixels of the first color and the minimum rectangle 244b encloses the largest connected area of pixels of the second color.

A representative property of each rectangle is used to characterize the motion of the operator's corresponding hand. In some embodiments, the center point of the rectangle, where two different diagonals of the rectangle intersect, is taken as the representative property. The center point 236a of the first rectangle and the center point 236b of the second rectangle are depicted. Each center point is represented by two values, an x-coordinate value and a y-coordinate value, such as a pixel column number and pixel row number, respectively, so the center point representative property is technically a vector property. In other embodiments, other properties of the rectangle are used as the representative property, including aspect ratio of rectangle width to height or area of the rectangle, alone or in some combination with or without the center point. Such a combination of property values also constitutes a vector representative property.

Figure 2D:
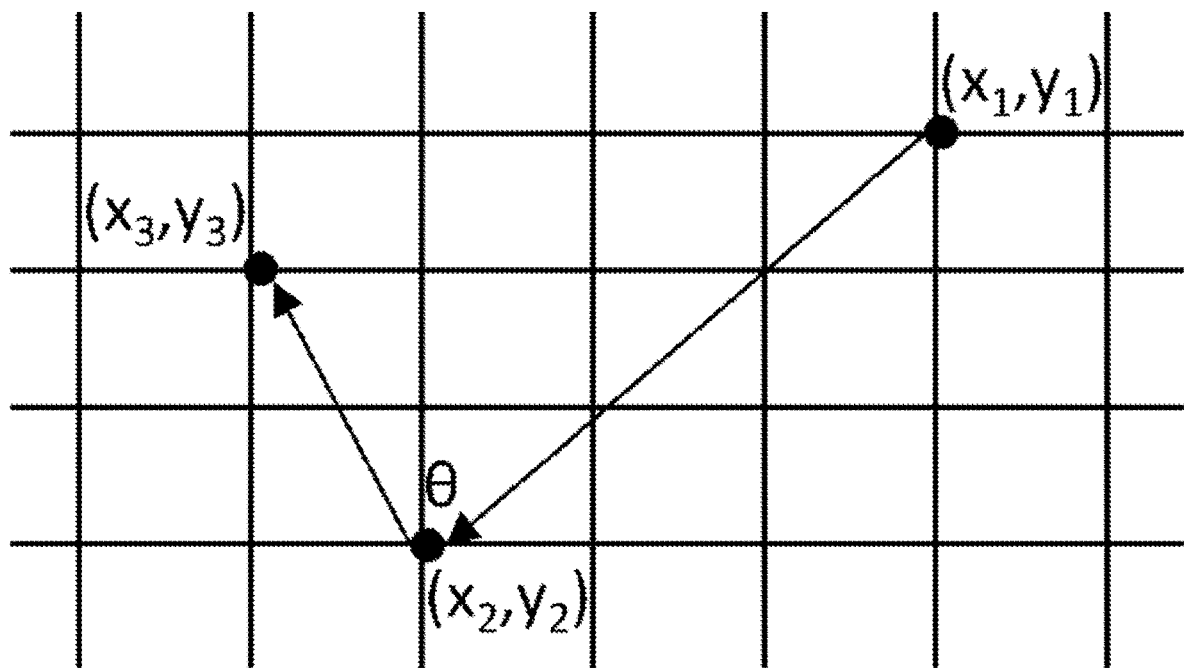
FIG. 2D is a diagram that illustrates an example time series of positions of a center point, as a representative property, of one minimum rectangle, according to an embodiment.

FIG. 2D is a diagram that illustrates an example time series of positions of a center point, as a representative property, of one minimum rectangle, according to an embodiment. Only three different center points are shown, corresponding to three different frames of the video data. The center point is shown to move from position value (x1, y1) to position value (x2, y2) to position value (x3, y3). The corresponding hand motion can be characterized by one or more parameters including: the position; the speed (the distance from (x1, y1) to (x2, y2) divided by the time difference between the two frames); the direction between (x1, y1) and (x2, y2); the acceleration (the difference between the speed from (x1, y1) to (x2, y2) and the speed from (x2, y2) to (x3, y3) divided by the time difference between two frames); and the angle change θ (the difference between the direction from (x1, y1) to (x2, y2) and the direction from (x2, y2) to (x3, y3)), among other parameters, or some combination. A time series is generated by values for one or more of these parameters at each of multiple different times corresponding to multiple different frames of the video data.

Figure 3:
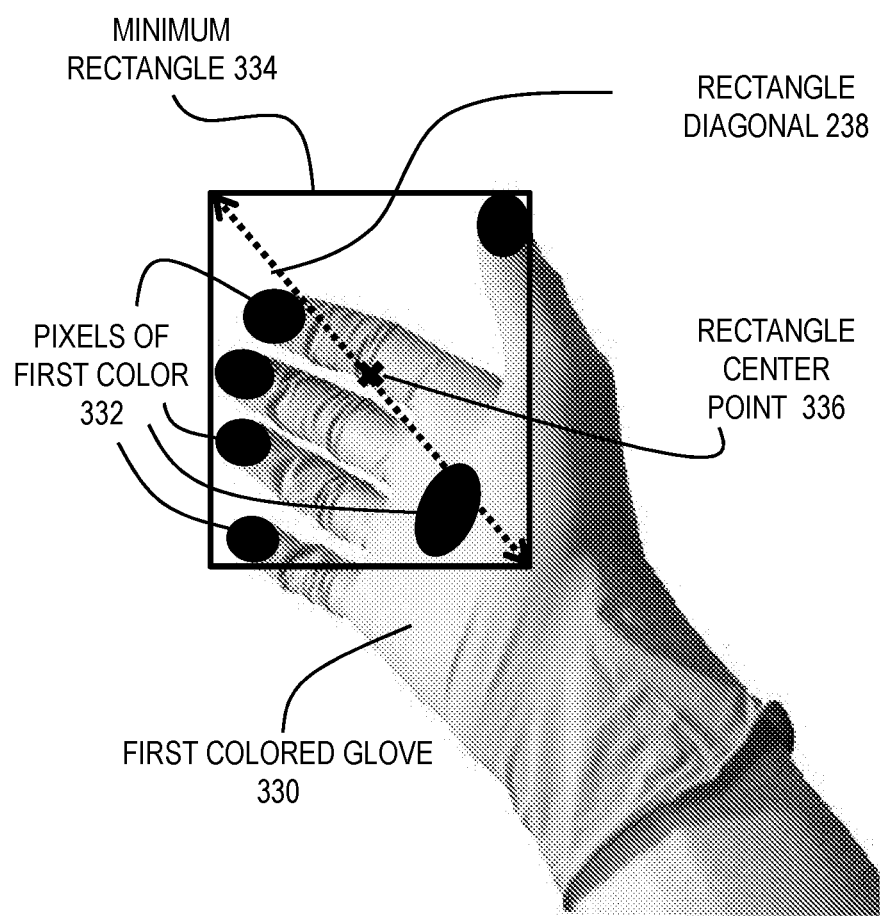
FIG. 3 is a diagram that illustrates a colored glove that is colored with a first color on only a portion of the glove, and the corresponding minimum rectangle, according to another embodiment.

In some embodiments, one entire glove is not the same color. FIG. 3 is a diagram that illustrates a colored glove that is colored with a first color on only a portion of the glove, and the corresponding minimum rectangle, according to another embodiment. An advantage of this coloring of a glove is that it places more weight on the movement of the fingers than on the center of the hand. This can provide a more subtle way to discriminate various operators, in some embodiments. In these embodiments, the size of the minimum rectangle is a representative property that is expected to be sensitive to the movement of the fingers. In some embodiments, the portion of the glove that is colored with a color of interest (either the first color or the second color) is connected, so that the largest minimum connected rectangle can be used. In some embodiments, the portion of the glove colored with the color of interest is disconnected. In some of these embodiments the minimum rectangle is the minimum rectangle including all connected rectangles that are above a minimum size, e.g., with a height greater than a threshold height and a width above a threshold width, as described in more detail below. This is done to prevent the minimum rectangle from including pixels caused by noise or clutter.

Figure 4A:
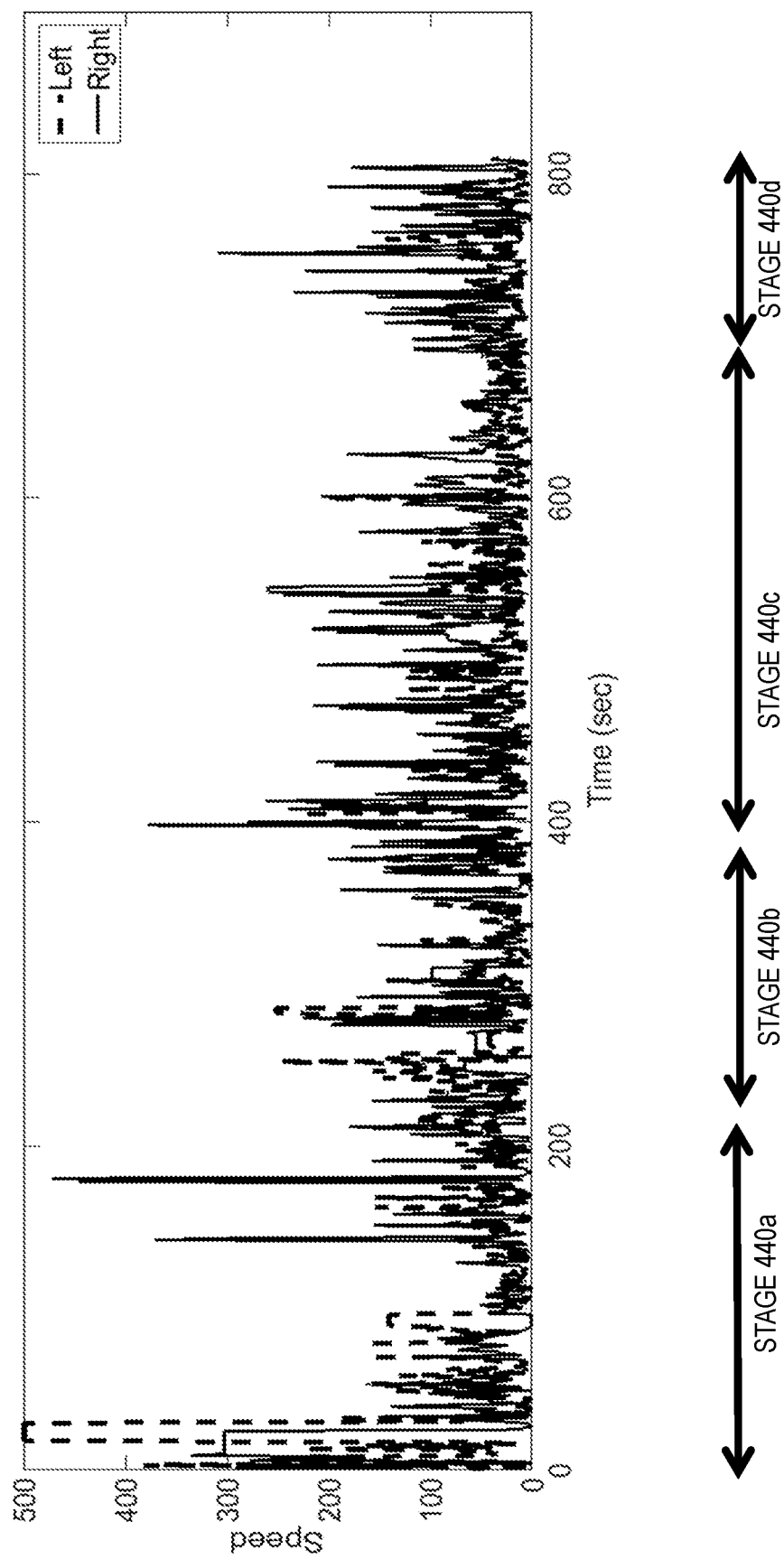
FIG. 4A through FIG. 4C are graphs that illustrate example time series of values of three parameters, respectively, two traces for each graph, each trace plotting values for one parameter based on a representative property of one minimum rectangle, according to an embodiment.
Figure 4B:
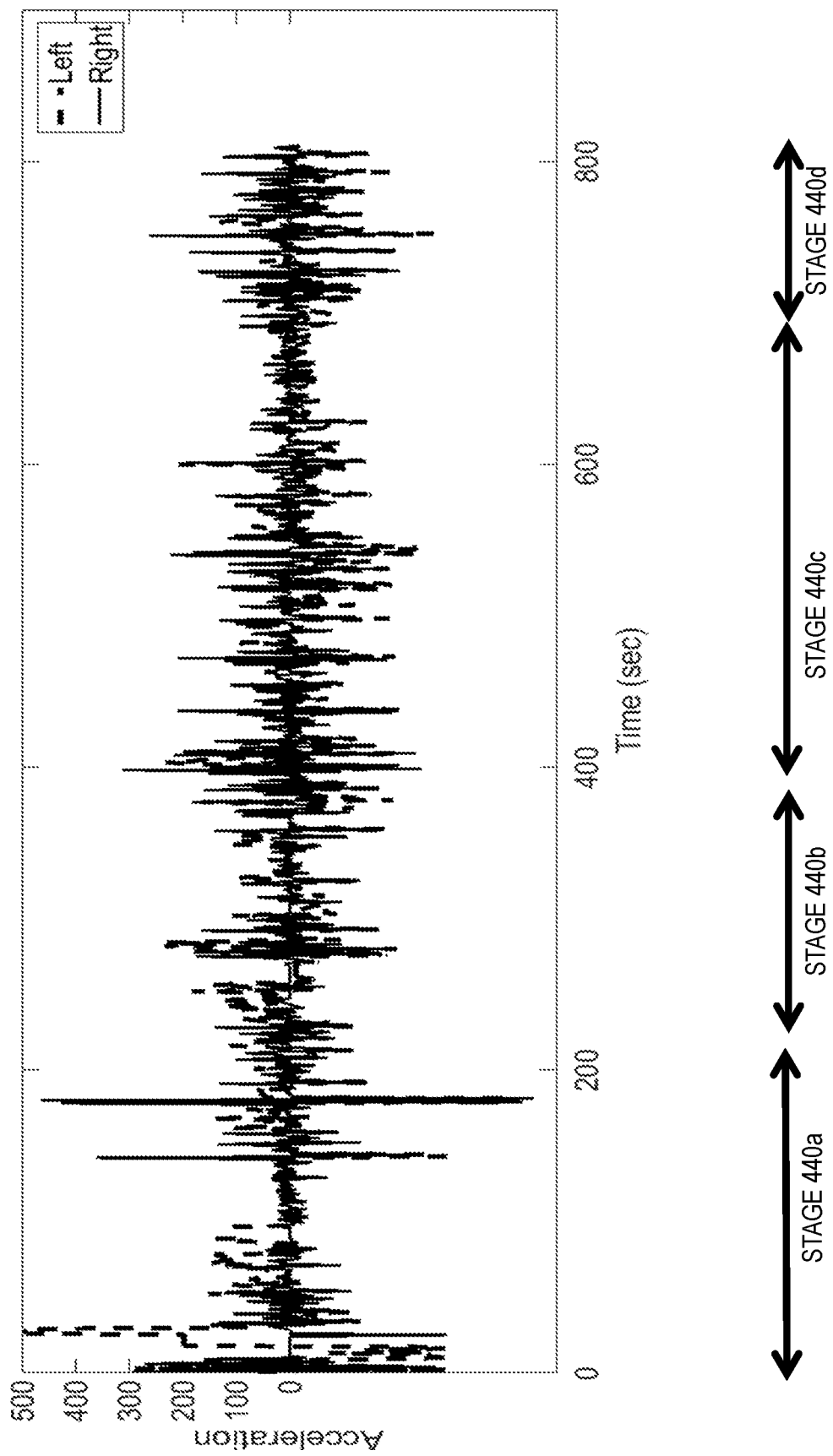
Figure 4C:
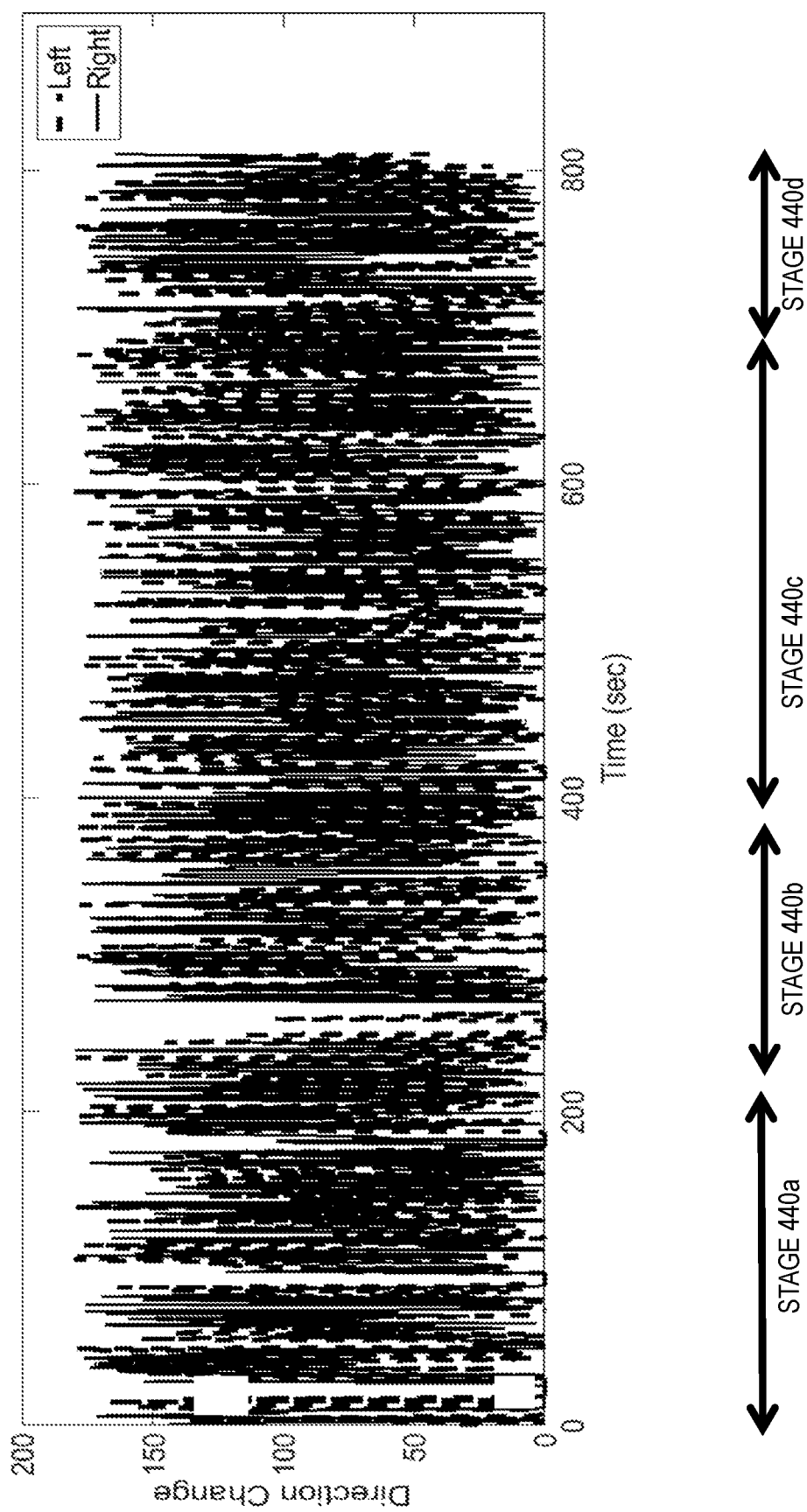

FIG. 4A through FIG. 4C are graphs that illustrate example time series of values of three parameters, respectively, two traces for each graph, each trace plotting values for one parameter based on a representative property of one minimum rectangle, according to an embodiment. On each graph, one trace represents the dominant hand and the second trace represents the non-dominant hand. FIG. 4A is a graph of a speed time series. The horizontal axis indicates time for a 13-minute time interval; the vertical axis indicates speed in arbitrary units. FIG. 4B is a graph of an acceleration time series. The horizontal axis is the same as in FIG. 4A, and the vertical axis indicates acceleration in arbitrary units. FIG. 4C is a graph of direction change time series. The horizontal axis is the same as in FIG. 4A, and the vertical axis indicates direction change in arbitrary units. During the 13 minutes of the surgical procedure represented by these time series, the surgical procedure progressed through several stages, such as a tool arranging stage, a skin preparation stage, a cutting stage, a spreading stage, a blunt dissection stage, a subcutaneous cutting stage, a manipulation stage, or a suturing stage, represented schematically by the time intervals for stage 440a through stage 440d indicated on each graph. Different procedures are expected to have different stages of different durations and different sequences. The degree of hand motion, even by an expert, is also expected to be different during different stages. Thus the measure of hand motion to distinguish expert from novice is expected to vary with stage of a procedure.

Entropy is a measure of the randomness of a series of numbers, e.g., how unpredictable a current value is based on the previous values. Thus, each of the above time series, as well as time series of other parameters used in other embodiments, or each stage thereof, can be characterized by a value of some measure of entropy.

Entropy was expected to discriminate between levels of surgical expertise, as entropy has been used previously in analysis of surgeon hand movements using synthetic surgical suture training models (Watson 2012). This is consistent with cognitive science research on motor learning showing a higher level of motor complexity in the trainee than the expert because learned motor skills are associated with a decrease in complexity of movement (Stergiou 2006). Dynamic systems theory of motor development emphasizes a reduction in variability as part of the learning process. Optimal movement variability balances the benefits of rigid control and randomness of movement; thus, a complexity measurement was expected to differ during training (Dosis 2005a). Neurophysiologically based accounts of skilled performance (Taylor 2014) separate strategic decision-making and execution skill.

However, none of the prior studies known to authors use hand-sensor-free methods; none used minimum rectangles of differently colored gloves; and none were studied during actual surgical procedures on living or dead subjects. Various entropy measures for time series, such as approximate entropy, sample entropy, Shannon joint entropy, Renyi joint entropy, or Tsallis joint entropy, or some combination, are suitable and available in the literature and in commercially available mathematics software packages.

Figure 5:
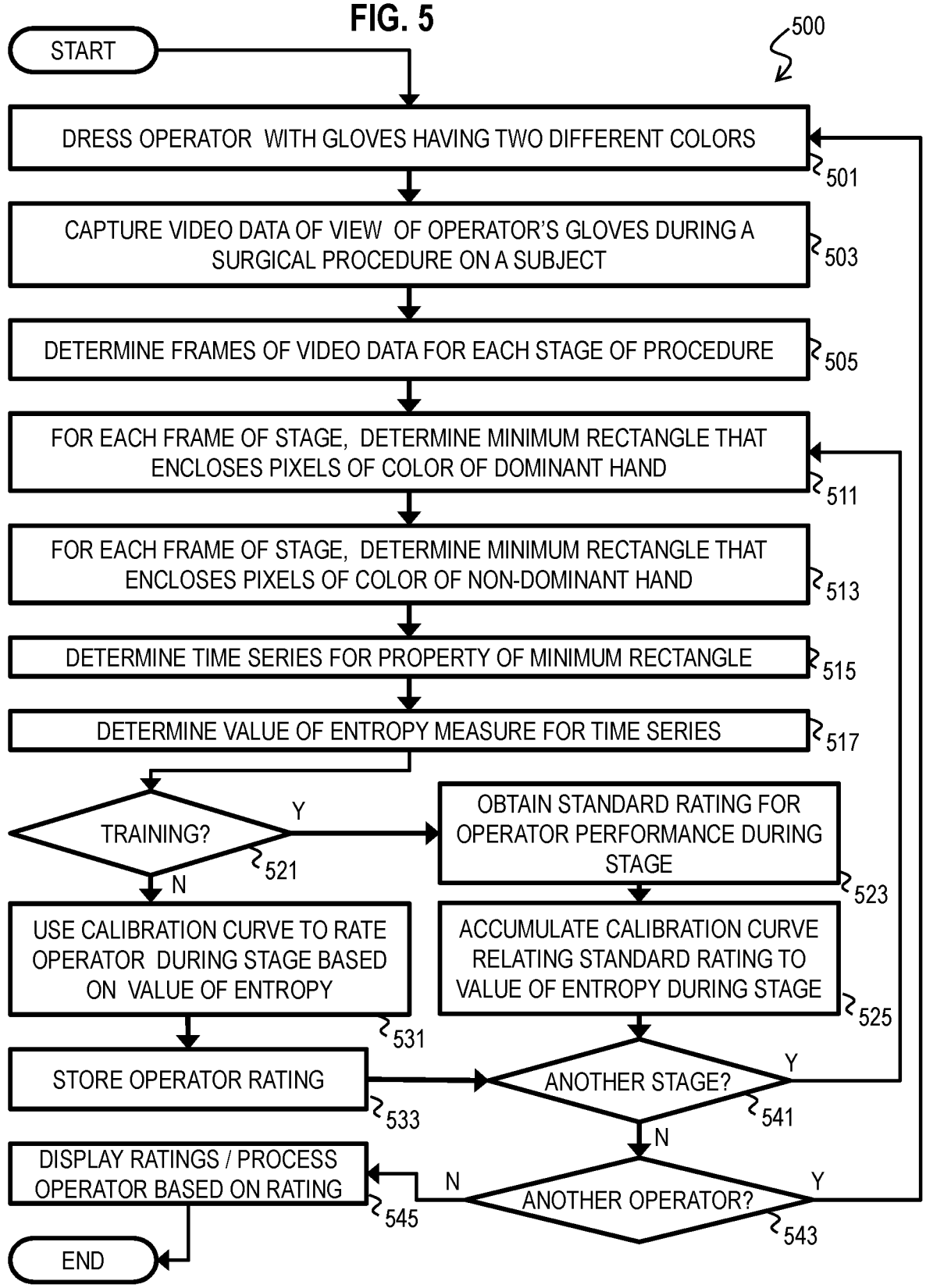
FIG. 5 is a flow chart that illustrates an example method for evaluating an operator's performance, according to an embodiment.

FIG. 5 is a flow chart that illustrates an example method 500 for evaluating an operator's performance, according to an embodiment. Although steps are depicted in FIG. 5 as integral steps in a particular order for purposes of illustration, in other embodiments one or more steps, or portions thereof, are performed in a different order, or overlapping in time, in series or in parallel, or are omitted, or one or more additional steps are added, or the method is changed in some combination of ways.

In step 501, an operator is dressed with surgical gloves having two different colors. At least one surgical glove has at least a portion that is colored with a first color selected to distinguish it from most other objects in a field of view of the operator's hands during a surgical procedure, including the gloves of another person operating on the subject. The portion colored must be large enough to be detected by the video camera and characterize the motion of the hand for the intended purpose. A glove with an example portion having the first color confined to the palm and last joint of each finger is depicted above in FIG. 3. An unnatural bright green or orange (popularly called fluorescent green or fluorescent orange) is a suitable color. In some embodiments, the glove with the first color is placed on the dominant hand of the operator. In some embodiments, the other glove has at least a portion that is colored with a different second color selected to distinguish it from most other objects in a field of view of the operator's hands during the surgical procedure. In some embodiments, the operator is a person of unknown skill to be evaluated. In some embodiments, used to calibrate the system, the operator is a person of known skill or experience. To ensure that the surgical procedure can be performed in a normal way, no other sensor is attached to either hand of the operator, so that the method is a hand-sensor-free method.

Thus, in various embodiments, step 501 includes dressing an operator with colored surgical gloves wherein a dominant hand of the operator wears a first surgical glove having a first color on at least a portion of the first glove and a non-dominant hand of the operator wears a second surgical glove having a different second color on at least a portion of the second glove. In some of these embodiments, the first color and the second color are each different from a color of any item that is not a surgical glove of the operator in the video data that views the operator's hands during the surgical procedure. In some of these embodiments, no sensor is attached to either hand of the operator.

In step 503, video data is captured of the operator's gloves during a procedure on a subject. In some embodiments, it is advantageous if the subject is a living subject or a once living subject, such as a cadaver, so that the operator can be evaluated under realistic settings and not under the artificial setting of a model or phantom. To compare the performance of several operators, including calibration of the system, it is advantageous in some embodiments to reduce variability among operators during the method 500. For example, it is advantageous in various embodiments for the lighting source 110 type or distance from the lighting source 110 to the hands of the operator during the procedure, or for the resolution of the video camera 120 or distance of the video camera 120 to the hands of the operator during the procedure, or some combination, to be held consistent for all operators subjected to the method 500. During step 503 the video data is sent to the computer system 140 via data channel 122 and stored on a computer-readable medium. Thus, in various embodiments, step 503 includes, after dressing the operator, capturing video data that views the operator's hands during a surgical procedure on a subject.

In step 505, the frames of the video data associated with each of one or more stages of the procedure are determined. In some embodiments, frames are taken at one rate (e.g., 12 frames per second) but only a subsample of the frames (e.g., 1 frame per second) is analyzed to reduce computational load and save total evaluation time. In some embodiments, every frame of the video data is considered to be in the same stage. This is advantageous when all operators are being evaluated on the same procedure. In some embodiments, step 505 is omitted and all frames of the video data are used.

An advantage of breaking up the video data into multiple stages is that operators performing different procedures can be compared by just comparing the stages common to both procedures. When the frames of the video data are divided among several stages, the time of the start of each stage can be determined in any manner known at the time, including manual and automatic means. In some embodiments, an evaluator watching the video data marks time when each stage begins. In some embodiments, the evaluator watches ancillary video, such as video from a head-mounted camera on the operator which shows the tools the operator is looking at and makes clear what tool is being wielded. In some embodiments, the operator is asked to wave his current tool at the video camera 120 to signal the next stage has begun. In some embodiments, the video camera includes a microphone and the video data include a sound recording. In some of these embodiments, the operator announces when each stage is beginning. For example, the operator states in a clear voice, "initial incision," "manual probing," "clamping," suturing," etc. Based on this announcement, either manually or automatically, the frames following are associated with the announced stage of the procedure. Thus, in step 505, the plurality of frames are confined to a time interval associated with a stage of the procedure, such as one or more of a tool arranging stage, a skin preparation stage, a cutting stage, a blunt dissection stage, a spreading stage, a subcutaneous cutting stage, a manipulation stage, or a suturing stage.

In step 511, each selected frame (e.g., every frame in the video data or the subset of sampled frames or the frames selected within only one stage of multiple stages) is automatically processed to determine a minimum rectangle that encloses the pixels within the range of digital values corresponding to the first color on the dominant hand of the operator. Various free or commercially available image processing software packages are available that can be tasked to perform this function in various embodiments. For example, Leap Motion SDK (San Francisco, Calif.), Matlab Image processing toolbox (Natick, Mass.), GNU Octave, and OpenCV can be used. In some embodiments, the rectangle that encloses all the pixels of the color of interest (one of either the first color or the second color) is determined. In some embodiments, the quality of the video may be low due to poor camera performance or lighting, or there may occur some background elements that closely match the color of interest, so that there is noise or clutter or both, and thus some random pixels for the color of interest. To hedge against such conditions, and to avoid the generation of unusually large rectangles produced by such noise that produce center points that may be unrelated to hand position, in some embodiments the minimum bounding rectangle (MBR) is determined that encloses a large percentage of the pixels of the first color, such as 75% or 90% or 95% or 99%, instead of all the pixels of the first color. For video data of sufficient quality, it is computationally advantageous to enclose 100% of the pixels, because such a rectangle is easily computed using the maximum and minimum row and column numbers of all the pixels having the first color.

In some embodiments the minimum bounding rectangle is defined by detecting all pixels of the first color and finding several minimum connected rectangles, each containing an entire connected space, then selecting the largest of the minimum connected rectangles. The selected minimum bounding rectangle for a color of interest is the minimum connected rectangle containing the largest connected space of pixels of the color of interest. It is advantageous in these embodiments to use a colored glove with a single connected area. In these embodiments, the correct area in the screen with the color of interest should be the largest area. However, there could be some noise in other places that may create other small rectangles. To select the minimum bounding rectangle that correctly indicates the hand, the minimum rectangle of connected pixels of the color of interest (one of the first or the second color) with the largest area is selected as the correct minimum rectangle.

In some embodiments there is only noise in a frame but no hand. To tackle this problem, a threshold is set for the smallest area that a minimum rectangle must have, to be considered as hand. In various embodiments, this threshold setting is empirical and determined by experiment. For example, based on the camera angle and distance to the operation area in the example embodiment, described below, a height threshold of a minimum bounding rectangle height was set as no less than $\frac{1}{15}^{th}$ of the image height, and a width threshold was set as no less than $\frac{1}{20}^{th}$ of the image width. In another embodiment, the thresholds could be extended (for wide range cover) to $\frac{1}{15}^{th}$ to $\frac{1}{25}^{th}$ in height, and $\frac{1}{15}^{th}$ to $\frac{1}{25}^{th}$ in width. These thresholds are also useful when the portion of the glove that has the color of interest is not connected, such as depicted in FIG. 3.

Thus step 511 includes, for each of a plurality of frames of the video data, automatically determining, on a processor, a minimum rectangle of pixels, called a first rectangle, which encloses pixels having the first color.

In step 513, each selected frame is automatically processed to determine a minimum rectangle that encloses the pixels within the range of digital values corresponding to the second color on the non-dominant hand of the operator, as described above for the dominant hand. In some embodiments, only the dominant hand is analyzed; step 513 is omitted.

In step 515, a time series is determined based on the selected frames in a current stage of one or more stages sampled by the video data. Each member of a first time series is a vector or scalar quantity that gives a value of one or more representative properties of the first minimum rectangle of the first color in one of the selected frames. For example, each member of the time series is a vector quantity that gives values of the x and y coordinates of the center of the rectangle or length and width of the rectangle, or a scalar quantity that gives a value of an aspect ratio or size or diagonal length of the minimum rectangle or speed or angle or acceleration magnitude or angle change among multiple rectangles in successive frames, among zero or more other properties of the minimum rectangle, or a vector quantity including multiple values for some combination of properties. Thus, in some embodiments, the representative property of the first rectangle is a center point of the first rectangle. The time of the time series member is the time of the video frame (or middle or average time of multiple video frames) for which the value or values for that member were determined. In some embodiments, a second time series is also determined. Each member of the second time series is a vector or scalar quantity that gives a value of one or more properties of the second minimum rectangle of the second color in one of the selected frames. Thus, step 515 includes determining automatically on a processor a first time series for a representative property of the first rectangle at the plurality of frames. Thus, in some embodiments, in step 515, the time series of the representative property is a time series of a set of one or more values, wherein the one or more values indicate one or more of position, speed, direction, acceleration magnitude or direction change of the center point.

In step 517, a value of entropy is determined for at least one time series. Entropy in its basic form is a measure of uncertainty. Specifically, the entropy of a random variable is a measure of the uncertainty associated with that random variable. When the entropy of a random variable is large this means that the uncertainty as to the value of that random variable is large, and vice versa (e.g., the expert has less random variability than the non-expert). The entropy of a series of values for a random variable is a function which attempts to characterize the "unpredictability" of a random variable, e.g., the degree to which the previous values do not predict the next value of the random variable. Any definition of entropy can be used, such as approximate entropy and sample entropy in various embodiments. In some embodiments, a joint entropy, or mutual information of the first time series and the second time series for the stage, in the form of Shannon entropy, Renyi entropy, or Tsallis entropy, or some combination, is computed. In some embodiments, a different entropy value is computed for each property of the time series, such as a measure of entropy in the time series of position, speed, acceleration magnitude or direction change, among others. Thus, step 517 includes determining automatically on a processor a first value for a first measure of entropy based on the first time series. In some embodiments a separate value for the measure of entropy is computed for the second time series of the minimum rectangles of the second color.

Step 521 represents a branch point that distinguishes subsequent processing based on whether the current value or values of entropy are for an operator being evaluated or a member of a training set for whom the level of experience or degree of expertise of the operator or both is known.

If the current value or values of entropy are for the training set, then control passes to step 523. In step 523, the standard rating for the operator performance for the current stage is obtained, e.g., an OSATS rating for the operator is obtained. Any method to obtain this rating may be employed in various embodiments, including retrieving from a local file or obtaining the data from a local or remote database either in response to a query message or unsolicited or by manual input from a human user of the system.

In step 525, the standard rating for the operator and the current value or values of entropy for the same operator are accumulated in a calibration curve. For example, a point is added to a multidimensional graph in which the first dimension is the standard rating and the other dimensions are the value or values of the entropy. After enough points are accumulated, a straight line or other simple curve is fit to the data points and a measure of goodness of fit is determined. In some embodiments, the graph and fits are updated after each point is added to the training set. The straight line or simple curve that shows a high goodness of fit is used as a calibration curve. As a result, an entropy value is used as a surrogate measure for the standard rating on the calibration curve that corresponds to the entropy value. In some embodiments a threshold entropy value on the curve is determined for each classification boundary on the standard rating dimension, e.g., to distinguish the untrained from the trained, the same individual at one or more intervals during training, different types of training, non-experts from those with experience and expertise, or to define competence using expert criteria. Thus, step 525 includes a metric of operator performance based at least in part on the first value for the first measure of entropy and providing a calibration curve, wherein the metric is based on the calibration curve that relates values of the first measure of entropy to values of independently assessed experience of an operator for a plurality of different operators during a training session. Control then passes to step 541, described below.

If the current value or values of entropy are for an operator being evaluated, then the path from the branch point 521 to step 531 is followed. In step 531, the calibration curve is used to provide a metric of operator rating based on the value of entropy. For example, the value of the entropy is used with the calibration curve to determine a rating value as a metric or a threshold. Entropy values are used to classify the operator according to one of the classifications, e.g., novice, experienced, or expert. In step 533, the operator rating determined in step 531 is stored on a computer-readable medium. Thus step 533 includes storing, on a computer-readable medium, a metric of operator performance based at least in part on the first value for the first measure of entropy. Control then passes to step 541.

In step 541, it is determined whether there is another stage to process within the video data. If so, then control passes back to step 511 and following steps where the next stage is the current stage. These steps determine the minimum rectangle or rectangles in each frame of the new current stage, and assemble the time series from all the frames in the current stage. If not, then control passes to step 543.

In step 543 it is determined whether there is another operator to videotape during a surgical procedure, either to add to the training set or to evaluate based on the calibration curve from the training set. If so, control passes back to step 501 and following step to dress the operator with the one or more colored gloves, videotape the operator during a surgical procedure, and determine the new minimum rectangles, time series and entropy. If not, control passes to step 545.

In step 545, the results of the rating process, either as the calibration curve or the rating of the evaluated operator, or both, are used. For example, data indicating the operator rating or calibration curve or both, for one or more stages, is presented on a display device. As another example, the operator is processed based on the rating. For example, the operator with a low rating is admitted to a training or remedial course, or decertified, or not hired for a position in a medical clinic, while an operator with a better rating is exempted from training or is certified or is hired for the position in the medical clinic.

These new hand-motion metrics, interval procedural timing and instrument use, using the method and system described above, can provide objective, less labor-intensive surgical performance evaluations and are a step to automated surgical technical skills assessment.

2. EXAMPLE EMBODIMENTS

According to an example embodiment, computer-based, sensor-free metrics for surgeon hand-motion entropy for certain stages of instrument use discriminate experts from residents and non-surgeon anatomists during open exposure and control of the axillary artery in cadavers. Metrics improve with training, deteriorate over time, and are congruent with a validated performance-based individual procedure score.

2.1 Axillary Artery (AA) Vascular Exposure on Cadaver

This embodiment compares results of entropy measures, timing and instrument use during axillary artery (AA) vascular exposure and control with previously validated individual procedure scores (IPS) (Mackenzie 2015) for each operator from video recordings analyzed by trained observers. This embodiment demonstrates that: 1) patterns of surgical hand movements, instrument use, duration of surgery and calculated joint entropy differ with expertise and training, and 2) these patterns during axillary artery exposure and control are congruent with performance-based validated IPS. Thus the sensor-free hand-motion entropy techniques perform well as an objective, quantitative indicator of operator performance.

The surgeon data reported here are a subset from a larger study examining surgical performance of exposure and control of peripheral vasculature before and after the Advanced Surgical Skills for Exposure in Trauma (ASSET) course. The ASSET course is a human cadaver-based 1-day course developed by the American College of Surgeons Committee on Trauma and adopted by military pre-deployment training platforms to teach surgeons to expose and control major blood vessels. Details of the larger study methods have been published (Mackenzie 2015; Shackelford 2015). Four participants in this report were also enrolled in the larger study.

For this preliminary analysis, the participating operators were asked to obtain vascular exposure and place a double vessel loop to gain proximal control of the AA for a simulated gunshot wound to the upper chest. The AA procedure was chosen to represent an ASSET course procedure for which performance metrics have been validated by the larger study (Mackenzie 2015), and because there is little anatomic body habitus variability for AA exposure.

Additionally, capturing unobstructed video of the AA procedure using an overhead camera was easier than for the other ASSET course peripheral vascular procedures. The AA procedure required an infraclavicular incision in the deltopectoral groove of a non-preserved human cadaver, spreading or incision of pectoralis major, dividing pectoralis minor about an inch (2.5 centimeters) inferior to the clavicle, and dissecting the structures and tissue overlying the AA, axillary vein and branches of the brachial plexus. Surgical procedures were performed in the State Anatomy Board laboratories at the University of Maryland in Baltimore.

The AA procedures were performed using a standardized set of 10 surgical instruments (scalpels, 3 types of retractors, 2 types of scissors, 2 types of forceps, and 2 types of clamps), following a script read by 2 co-located evaluators. The AA script to obtain the IPS score included a patient scenario, patient management knowledge questions, and marking of the planned surgical incision, followed by completing the indicated procedure. IPS included binary answers for knowledge questions and checklists for procedural steps, Likert scales for surgical technical skills, and error identification (Shackelford 2015). In previously reported studies (Shackelford 2015), the IPS tool was evaluated for resident surgeons included in this study before and within 2 weeks of completing the ASSET course and was repeated a year and 18 months after ASSET training to assess skill retention.

The cadaver laboratories were equipped with pan-tilt zoom cameras mounted on the ceiling directly above each cadaver table (Vaddio Ceiling View 70 PTZ Camera Vaddio, Minnetonka, Minn.) and an infrared (IR) imaging camera and analysis system (ICI 9640 P, Infrared Cameras Inc., Beaumont, Tex.). Video recordings, obtained from a head-mounted camera (Looxcie LX2 Looxcie, Inc., Sunnyvale, Calif.) worn by the surgeon, enabled analysis when the surgeon's head obstructed the pan-tilt zoom camera's view of the surgical region of interest. Continuous video images were collected in which the surgical incision and the operator's hands, arms, and torso were visible, without obstruction of the camera line-of-sight view. The camera used for entropy data collection (Nikon D600 Model) collected video at 50 frames per second (fps), and had a 50 to 80 degrees unobstructed field of view including a region of interest of the incision and the operator's hands.

A panel of trauma experts was consulted for assistance in the development of the AA procedural analyses as previously described (Mackenzie 2015; Shackelford 2015). The experts provided feedback on metrics that might differentiate between novice and experienced surgeons. Other possible hand-motion metrics were obtained from review of the existing literature (Ahmidi 2015; D'Angelo 2015; Datta 2001, 2006; Dosis 2005a; Gray 2012; Moorthy 2003; Overby 2014; Uemura 2014; Watson 2012, 2014). Joint entropy (of right and left hands together) was used to quantify and summarize the motion chaos of hand-movements.

Two expert operators had an average of 20 years surgical clinical practice at Level-1 trauma centers. Post-graduate year (PGY) 3 and PGY 5 resident surgeons who had participated in the larger study were selected as intermediate operators based on their change in IPS to assess congruencies between hand-motion and technical skill. Two PhD anatomists were selected as less-experienced operators. The two anatomist operators and one expert operator did not receive an IPS score as they were already trained as IPS evaluators for the larger study. The anatomist operators did not take the ASSET course but received surgical instruction on the AA procedure as their training.

Video recordings were available for the two surgical residents performing the AA procedure before and after ASSET training and 12 or 18 months later for skill retention evaluation, when they wore colored surgical gloves. Both experts were ASSET instructors and one wore colored gloves during AA procedure video recording. One anatomist was video-recorded performing the AA procedure before and after training wearing colored gloves. Joint entropy data were obtained for the five AA procedures in which colored gloves were worn.

Two trained video reviewers independently reviewed all video recordings, whether or not the operators wore colored gloves, to obtain the instrument use and AA procedure timing data. Video was reviewed frame-by-frame using VirtualDub (version 1.10.4), a free video processing program, and each start and stop time, active and idle time associated with blunt dissection and instrument usage was recorded from skin incision to passage of the vessel loop as human-observable alternative measures to the objective entropy computations. Start time was identified when a hand or surgical instrument made contact with the cadaver. Stop time was identified when the hand or instrument left contact with the cadaver. Active time was calculated as the sum of duration of the activities of each hand independently using instruments and blunt dissection time. Ratios of active to idle time were also calculated. Idle time was defined as the time instruments spent outside the surgical incision for more than one second. Any reason for idle time, such as to organize instruments, was noted. A software script was written to sum active times for each instrument and for blunt dissection, as well as total active and idle times for each participant.

The two video reviewers compared their timing results. Any discrepancies of 5 s or more were reviewed together, and times were agreed upon by consensus. Nine metrics (all non-entropy alternatives to entropy-based metrics of method 500) were gathered: 1) total time (skin incision to passage of vessel loop); 2) total idle time; 3) total active time; 4) ratio of active time to idle time; 5) time from skin incision to division of pectoralis minor; 6) number of times instruments changed; 7) blunt dissection time; 8) sharp dissection time; 9) instrument organization before surgery.

In five instances, operators wore color-coded gloves to allow computer hand-motion feature extraction by computer vision algorithms without attaching hand-sensors using the method 500 of FIG. 5. Left and right hand position for each frame was extracted from color-coded surgical gloves (green, dominant hand; orange, non-dominant hand) using the OpenCV (Python) library to detect glove colors (as shown for one frame in FIG. 2B). The centers of the minimum rectangular boxes defined by the glove colors were calculated for each video frame to define the position of the hand time series with a temporal resolution of 1 second, to be used to calculate time series of other representative properties consisting of speed (pixel widths change per second), acceleration (change in speed per second), and change of direction θ (degrees). The change of direction θ was quantified by the angle formed by two consecutive movement directions, as shown in FIG. 2D. Hand motion entropy data were calculated by using Shannon joint hand-motion entropy using the formula given by Equation 1.

$$H(X,Y) = -\Sigma p(x,y) \log_2 p(x,y) \quad (1)$$

where H denotes joint entropy, X, Y denote the representative property of left- and right-hand motion, x and y indicate the time series values of the representative property for the left and right hands, respectively, and the summation is over all the frames of the time series for the stage under consideration. Entropy measures were compared between operators during AA procedures.

Training levels and timing of hand-tracking motion data collection are shown in Table 1. The head-camera would not allow automated tracking of the color-coded gloves from these images due to constant head movement, but these head-camera images were useful for evaluations linked to IPS, and to show which instruments were picked up from the instrument cart. Results for entropy measures of color-coded glove movement among with other non-entropy measures of hand motion are described in Table 2.

TABLE 1

Timing of video records, state of training, and colored-glove/hand-motion data availability for each study participant.

|  | Pre-Training | Post-Training | Skill Retention |
| --- | --- | --- | --- |
| Anatomist 1 | 0 | X | 0 |
| Anatomist 2 | + | + | 0 |
| Resident PGY 5 | X | X | + |
| Resident PGY 3 | X | X | + |
| Expert 1 | 0 | 0 | X |
| Expert 2 | 0 | 0 | + |

X: performed the AA procedure without automated hand motion data extractions
+: performed the AA procedure with color-coded gloves to obtain automated hand motion data
0: no video available

TABLE 2

Metrics derived from observational video analysis.

|  | Anatomists n = 2 | Experts n = 2 | Residents Pre-Training n = 2 | Resident Post-Training n = 2 | Resident Retention n = 2 |
| --- | --- | --- | --- | --- | --- |
| Total Time in seconds | 625 | 177 | 1200 | 378 | 426 |
| Idle Time in seconds | 46 | 9 | 60 | 29 | 36 |
| Number Instrument change | 45 | 23 | 97 | 35 | 50 |
| Time to Pec. Min. Incision | 99 | 64 | 842 | 100 | 120 |
| IPS Score | NA | 79% | 49% | 75% | 62% |
| Joint Entropy (Speed/ Acceleration/ Direction) |  9.15/ 9.17/ 3.29 | 7.29/ 7.31/ 3.25 | NA | 8.55/ 8.62/ 3.36 | 8.47/ 8.63/ 3.40 |

Resident Retention = data obtained 12 or 18 months after training.
Values are shown as means.
NA = not available.
Joint entropy Speed = pixelwidths/second;
acceleration = change in speed/second;
Directional change = degrees On average, experts had lower active, idle, and total times, the highest ratio of active to idle times, lower blunt and sharp dissection times, and shorter time to divide pectoralis minor, while the pre-training residents had the higher total time, active time, and time to pectoralis minor and longest sharp dissection time and a greater number of instrument changes. Anatomists had the longest blunt dissection time. Active time decreased after training by an average of 554 seconds for residents and 303 seconds for anatomists. When re-evaluated one year or 18 months later the resident's active time was longer. During active operating time, pre-training surgical residents changed instruments on average 97 times, compared to 35 times after training and 50 times when evaluated one year or 18 months later. The average of the two expert instrument changes was 23, while the pre-training anatomist had 89 instrument changes; after training the anatomists averaged 45 instrument changes. The pre-training residents had the longest time to pectoralis minor, >1200 seconds (s), because they both failed to expose and divide pectoralis minor within the 20-minute time limit. However, in post-training, both residents successfully divided pectoralis minor in an average time of 120 s. The anatomists' time to divide pectoralis minor was 497 s prior to training and 199 s after, compared to the experts' average time of 64 s. Both pre-training anatomists and residents failed to organize their instruments prior to starting the procedure, whereas the experts did. The expert's IPS score was 79%. Pre-training residents' IPS was 49%, which increased to 75% post-training, as per their selection for this study. Residents' average skill-retention evaluation IPS scores were 62%, lower than immediately after the ASSET course. These non-entropy based metrics obtained from manual video analysis were in concordance with IPS changes with training and skill retention evaluations.

Automatic detection of instrument use, e.g., for stage discrimination, was not successful. Tracking duration of use of the 10 different types of instruments obtained from video analysis showed that different operators used different instruments. Anatomists had very different instrument selection than expert surgeons. Anatomists used Debakey forceps much of the time to spread tissue and relied on left- and right-handed blunt dissection. Anatomists also had greater duration of use for the vessel loop and army-navy retractor than the surgeons. Expert surgeons recorded shorter duration of blunt dissection than residents but spent a greater proportion of their operating time using blunt dissection. Among the two experts and two resident surgeons, the mean ratio of sharp to blunt dissection time was 1:2.4 (experts) compared to 1:7.3 for the residents before ASSET and 1:4.5 for the same residents after training.

Examples of speed, acceleration and direction time series are illustrated in FIG. 4A through FIG. 4C, described above. The joint entropy data are shown in Table 2. Calculated speed, acceleration, and direction joint entropy were least with the experts, distinguishing the experts from the residents and anatomists. The entropy analyses correlate with IPS, the timing metrics during AA procedure, and with the level of experience and training.

These embodiments demonstrates that use of the color-coded gloves without additional hand sensors 1) did not interfere with the surgeons' hand movements and 2) provided sufficient color contrast to allow automated tracking by the computer software. It was found that expert surgeons' hand movements as measured by entropy of minimum square representative property time series for several properties automatically differentiate expert surgeons from residents and anatomists performing an AA procedure. Joint hand-motion entropy detected differences in anatomist's hand-motion before and after training in the AA procedure.

Video-analyses of instrument use and timing of AA procedures, when color-coded gloves were not worn, were in agreement with both the joint entropy data (when color-coded gloves were worn) and the IPS (when available). The congruence of these data relating experience, timing metrics, instrument use and an IPS performance based score to hand-motion joint entropy suggests that a fully automated assessment of open surgical technical skills is possible using colored gloves and one or more properties of minimum rectangles enclosing the coded colors. Automatic, objective assessments of surgeon performance are enabled, in real-time or post hoc, by extracting surgeon hand-motion data from intra-operative video recordings when using color-coded gloves with as few as one color per glove.

The approach presented here offers the benefit of not requiring any physical sensors. Cadavers provide more accurate representation of an operating room anatomy experience than phantoms or models, making cadaver subjects an advantageous choice for this study. However, the surgeons were not under stress as occurs in a busy trauma center, and there was no bleeding, hematoma or tissue damage as there would be in live clinical situations, making dissection and anatomic structural recognition easier than in real life. The approach used here is readily adapted to the more realistic circumstances of a live subject as well, because there are no sensors on the operator's hands to inhibit the best possible conditions for the subject's benefit. For the purpose of a feasibility study, cadavers are a good compromise. Further advantageously, the use of color-coded gloves and video capture can also be used in clinical surgical scenarios. The participants also operated without guidance or instruction, having to find and choose their own instruments in contrast to a real operative procedure situation. This is advantageous because it isolates the expertise of the operator and does not confound the experience of a senior surgeon providing guidance during clinical surgeries.

2.2 Other Example Embodiments

In some embodiments, more even distribution of lighting to minimize shadows is used. This offers the advantage of improving the ability of software detection of color-coded gloves.

The gloves used in the above example embodiment were non-sterile and were loose fitting. For clinical surgery embodiments on living subjects, the gloves are color-coded but are also sterile and fitted with a matte finish.

In some embodiments, cameras with a higher frame rate (60 fps) and a resolution of 1280×720 would improve the fidelity of hand-motion detection. Fixed camera position and direction from the incision that provide a view of the hands unobstructed by assistants would standardize video data collection and entropy calculations in some embodiments.

In some embodiments, a head-mounted camera helps analysis of hand motion, by functioning as an eye-tracker of the operating surgeon's attention. The head-mounted camera allows increased situational awareness of the context of instrument use, e.g., stage of the procedure, and other events that may impact surgeon hand motion, such as technical details of bleeding and anatomic structures in the surgical site, that are not available from a fixed overhead camera. The inexpensive (about $150) and lightweight LOOXCIE™ camera was found to have sufficient memory to store up to 75 minutes of video at 640×480 at 30 fps, and attached easily to a headset. The audio quality was excellent and allowed accurate transcription of communications.

In some embodiments, an infrared camera has potential for use in the cadaver laboratory, as it clearly differentiates the surgeon from the cadaver and instruments. However, it is expensive ($9,950), and surgical instruments warm as they are used. The temperature discrimination between cadaver and surgeon would not be present in live patients during clinical operations, so some infrared signature is added to the gloves in these embodiments. However, the instruments are more readily distinguished from the gloved hands using an infrared camera, and the infrared data can be used to determine the duration of various stages of the surgical procedure.

3. COMPUTATIONAL HARDWARE OVERVIEW

Figure 6:
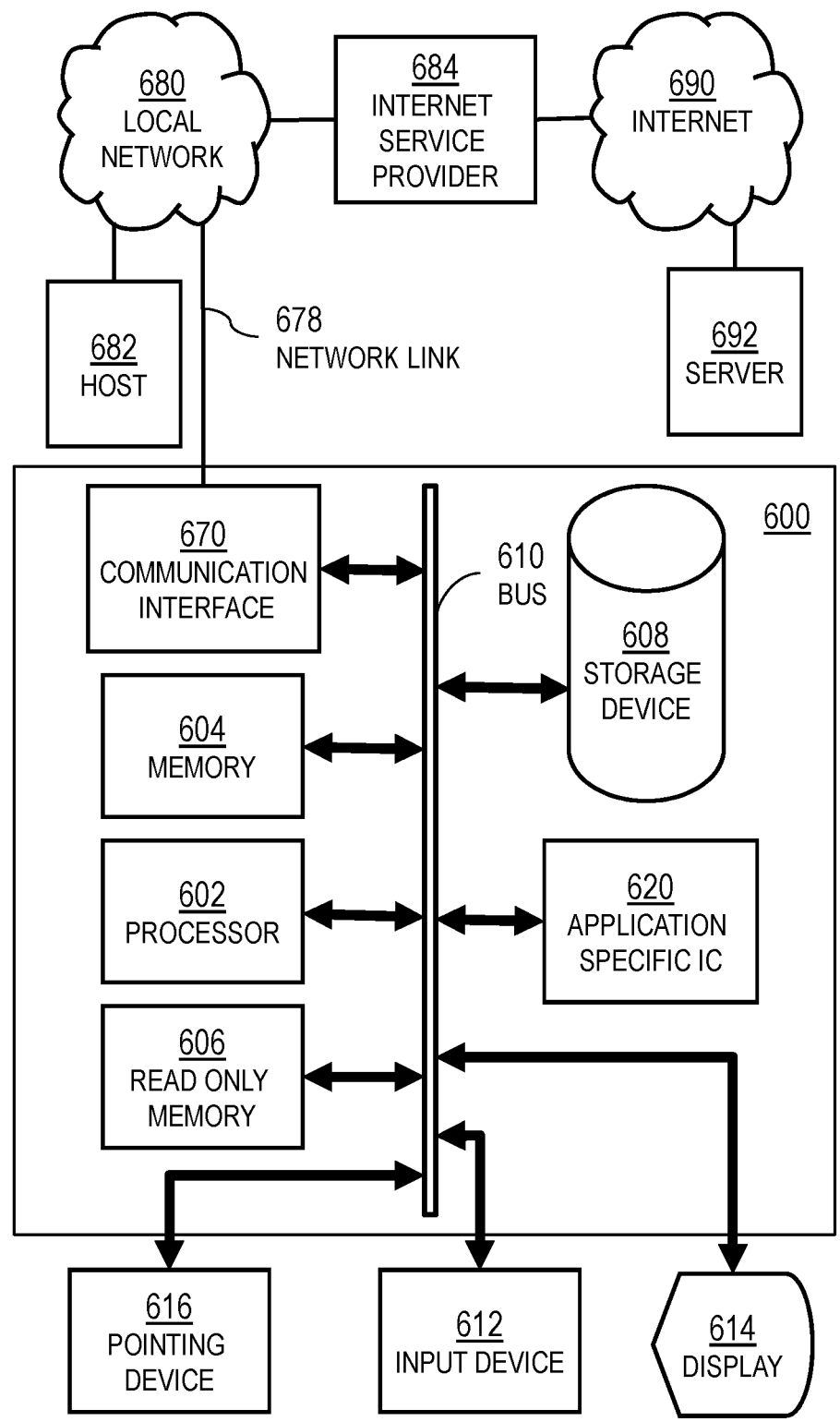
FIG. 6 is a block diagram that illustrates a computer system upon which an embodiment of the invention may be implemented.

FIG. 6 is a block diagram that illustrates a computer system 600 upon which an embodiment of the invention may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps of one or more methods described herein.

A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitutes computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. Carrier waves, such as acoustic waves and electromagnetic waves, including radio, optical and infrared waves, travel through space without wires or cables. Signals include man-made variations in amplitude, frequency, phase, polarization or other physical properties of carrier waves. For wireless links, the communications interface 670 sends and receives electrical, acoustic or electromagnetic signals, including infrared and optical signals, that carry information streams, such as digital data.

The term computer-readable medium is used herein to refer to any medium that participates in providing information to processor 602, including instructions for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 602, except for carrier waves and other signals.

Logic encoded in one or more tangible media includes one or both of processor instructions on a computer-readable storage media and special purpose hardware, such as ASIC 620.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware such as application specific integrated circuit 620 may be used in place of or in combination with software to implement the invention. Thus, embodiments of the invention are not limited to any specific combination of hardware and software.

The signals transmitted over network link 678 and other networks through communications interface 670 carry information to and from computer system 600. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a signal on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infrared transmitter to convert the instructions and data to a signal on an infrared carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

Figure 7:
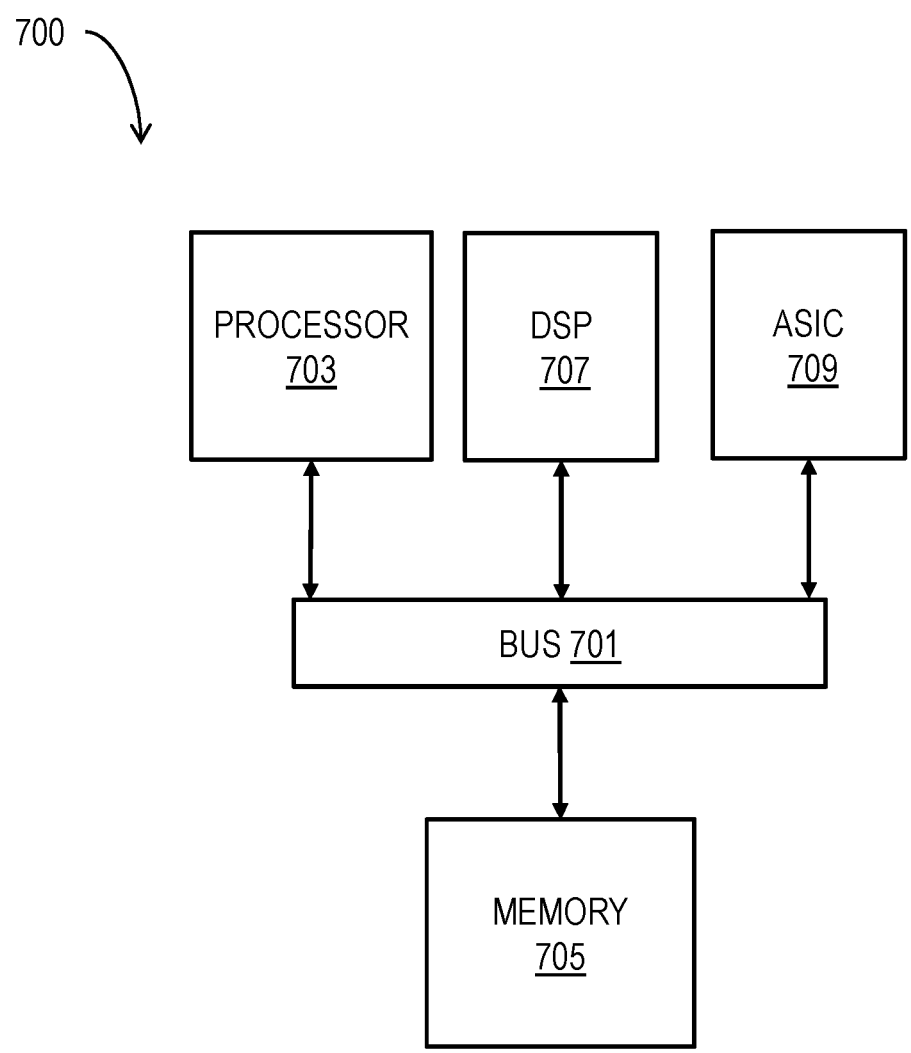
FIG. 7 illustrates a chip set upon which an embodiment of the invention may be implemented.

FIG. 7 illustrates a chip set 700 upon which an embodiment of the invention may be implemented. Chip set 700 is programmed to perform one or more steps of a method described herein and includes, for instance, the processor and memory components described with respect to FIG. 6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 700, or a portion thereof, constitutes a means for performing one or more steps of a method described herein.

In one embodiment, the chip set 700 includes a communication mechanism such as a bus 701 for passing information among the components of the chip set 700. A processor 703 has connectivity to the bus 701 to execute instructions and process information stored in, for example, a memory 705. The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 705 also stores the data associated with or generated by the execution of one or more steps of the methods described herein.

4. ALTERATIONS, EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the items, elements or steps modified by the article.

5. REFERENCES

Ahmidi, N., P. Poddar, J. D. Jones, et al. 2015. Automated objective surgical skill assessment in the operating room from unstructured tool motion in septoplasty. Int J Comput Assist Radiol Surg 10 (6): 981-991.

Cao, C. L., P. Milgram. 2006. Direction and location are not sufficient for navigating in nonrigid environments: an empirical study in augmented reality. Presence: Teleop Virt 16 (6): 584-602.

D'Angelo, A. L., D. N. Rutherford, R. D. Ray, et al. 2015. Idle time: an underdeveloped performance metric for assessing surgical skill. Am J Surg 209 (4): 645-651.

Datta, V., S. Mackay, M. Mandalia, A. Darzi. 2001. The use of electromagnetic motion tracking analysis to objectively measure open surgical skill in the laboratory-based model. J Am Coll Surg 193 (5): 479-85.

Datta, V., S. Bann, M. Mandalia, A. Darzi. 2006. The surgical efficiency score: a feasible, reliable, and valid method of skills assessment. Am J Surg 192 (3): 372-378.

Digioia, A. M., D. Simon, B. Jaramaz, et al. 1995. HipNav: Pre-operative planning and intra-operative navigational guidance for acetabular implant placement in total hip replacement surgery. Proc Comp Assis Ortho Surg Symposium (CAOS), Bern.

Dosis, A., R. Aggarwal, F. Bello, et al. 2005a. Synchronized video and motion analysis for the assessment of procedures in the operating theater. Arch Surg 140 (3): 293-299.

Dosis, A., F. Bello, D. Gillies, et al. 2005b. Laparoscopic task recognition using Hidden Markov Models. Stud Health Technol Inform 111: 115-122.

Gambadauro, P., and A. Margos. 2012. Surgical videos for accident analysis, performance improvement, and complication prevention: time for a surgical black box?. Surg Innov 19 (1): 76-80.

Gray, R. J., K. Kahol, G. Islam, et al. 2012. High-fidelity, low-cost, automated method to assess laparoscopic skills objectively. J Surg Educ 69 (3): 335-339.

Kranzfelder, M., A. Schneider, H. Feussner, et al. 2013. Shock/Sepsis/Trauma/Critical Care: Real-time instrument detection in minimally invasive surgery using radiofrequency identification technology. J Surg Res 185 (2): 704-710.

Mackenzie, C. F., E. Garofalo, S. Shackelford, et al. 2015. Using an Individual Procedure Score before and after the advanced surgical skills exposure for trauma course training to benchmark a hemorrhage-control performance metric. J Surg Educ (July 23); pii: S1931-7204(15)00161-0. doi: 10.1016/j.jsurg.2015.06.009. [Epub ahead of print]

Martin, J. A., et al. 1997. Objective structured assessment of technical skill (OSATS) for surgical residents. Br J Surg 84 (2): 273-278.

Moorthy, K., Y. Munz, S. K. Sarker, A. Darzi. 2003. Objective assessment of technical skills in surgery. BrMed J 327 (7422): 1032-1037.

Overby, D., R. Watson. 2014. Hand motion patterns of fundamentals of laparoscopic surgery certified and non-certified surgeons. Am J Surg 207 (2): 226-230.

Reiley, C. E., G. D. Hager. 2009. Task versus subtask surgical skill evaluation of robotic minimally invasive surgery. Proceedings of the 12th International Conference on Medical Image Computing and Computer-Assisted Intervention (MICCAI), Part I. Springer: Berlin; 435-442.

Shackelford, S., E. Garofalo, V. Shalin, et al. 2015. Development and validation of traumatic surgical skills metrics: Preliminary assessment of performance after training. J Trauma Acute Care Surg 79 (1): 105-110.

Stergiou, N., R. Harbourne, J. Cavanaugh. 2006. Optimal movement variability: a new theoretical perspective for neurological physical therapy. J Neurol Phy Ther 30: 120-129.

Taylor, J. A., R. B. Ivry. 2014. Cerebellar and prefrontal cortex contributions to adaptation, strategies, and reinforcement learning. Frog Brain Res 210: 217-253.

Uemura, M., M. Tomikawa, R. Kumashiro, et al. 2014. Analysis of hand motion differentiates expert and novice surgeons. J Surg Res 188 (1): 8-13.

Watson, R. A. 2012. Computer-aided feedback of surgical knot tying using optical tracking. J Surg Educ 69 (3): 306-310.

Watson, R. A. 2014. Use of machine learning algorithm to classify expertise: analysis of hand motion patterns during a simulated surgical task. Acad Med 89 (8): 1163-1167.

Zappella, L., B. Béjar, G. D. Hager, R. Vidal. 2013. Surgical gesture classification from video and kinematic data. Med Image Analysis 17 (7): 732-745.

What is claimed is:

1. A method comprising:
dressing an operator with colored surgical gloves wherein a dominant hand of the operator wears a first surgical glove having a first color on at least a portion of the first glove and a non-dominant hand of the operator wears a second surgical glove having a different second color on at least a portion of the second glove;
after dressing the operator, capturing video data that views the operator's hands during a surgical procedure on a subject;
for each of a plurality of frames of the video data, automatically determining, on a processor, a minimum rectangle of pixels, called a first rectangle, that encloses pixels having the first color;
determining automatically on a processor a first time series for a representative property of the first rectangle at the plurality of frames;
determining automatically on a processor a first value for a first measure of entropy based on the first time series; and
storing, on a computer-readable medium, a metric of operator performance based at least in part on the first value for the first measure of entropy.

2. A method as recited in claim 1, wherein no sensor is attached to either hand of the operator.

3. A method as recited in claim 1, wherein the first color and the second color are each different from a color of any item that is not a surgical glove of the operator in the video data that views the operator's hands during the surgical procedure.

4. A method as recited in claim 1, further comprising providing a calibration curve, wherein the metric is based on the calibration curve that relates values of the first measure of entropy to values of independently assessed experience of an operator for a plurality of different operators during a training session.

5. A method as recited in claim 1, wherein the plurality of frames are confined to a time interval associated with a stage of the procedure, such as one or more of a tool arranging stage, a cutting stage, a spreading stage, a subcutaneous cutting stage, a manipulation stage, or a suturing stage.

6. A method as recited in claim 1, wherein the subject is alive during the surgical procedure or was once alive before the surgical procedure.

7. A method as recited in claim 1, wherein the representative property of the first rectangle is a center point of the first rectangle.

8. A method as recited in claim 7, wherein the time series of the representative property is a time series of a set of one or more values, wherein the one or more values indicate one or more of position, speed, direction, acceleration magnitude or direction change of the center point.

9. A method as recited in claim 1, wherein:
the method further comprises
for each of the plurality of frames of the video data, automatically determining, on a processor, a minimum rectangle of pixels, called a second rectangle, that encloses pixels having the second color,
determining automatically on a processor a second time series of a representative property of the second rectangle at the plurality of frames, and
determining automatically on a processor a second value for a second measure of entropy based on the second time series; and
the metric of operator performance is based at least in part on the second value for the second measure of entropy.

10. A method as recited in claim 9, wherein the second measure of entropy is joint entropy of the first time series and the second time series.

11. A method as recited in claim 1, wherein the first rectangle is a largest rectangle of one or more minimum connected bounding rectangles that each encloses a connected area of pixels of the first color.

12. A method as recited in claim 11, wherein the first rectangle has a height that is at least a threshold height and a width that is at least a threshold width.

13. A method as recited in claim 1, wherein the first rectangle is a minimum bounding rectangle that encloses every minimum connected bounding rectangle that each encloses a connected area of pixels of the first color and has a height that is at least a threshold height and a width that is at least a threshold width.

14. An apparatus comprising:
a computer-readable medium;
at least one processor; and
at least one memory including one or more sequences of instructions,
the at least one memory and the one or more sequences of instructions configured to, with the at least one processor, cause the apparatus to perform at least the following:
capturing video data that views an operator's hands during a surgical procedure on a subject, wherein a dominant hand of the operator wears a first surgical glove having a first color on at least a portion of the first glove and a non-dominant hand of the operator wears a second surgical glove having a different second color on at least a portion of the second glove;
for each of a plurality of frames of the video data, automatically determining, on a processor, a minimum rectangle of pixels, called a first rectangle, that encloses pixels having the first color;
determining automatically on a processor a first time series for a representative property of the first rectangle at the plurality of frames;
determining automatically on a processor a first value for a first measure of entropy based on the first time series; and
storing on the computer-readable medium a metric of operator performance based at least in part on the first value for the first measure of entropy.

15. A system comprising:
the apparatus as recited in claim 14; and
a video camera disposed to view the operator's hands during the surgical procedure and collect the video data.

16. A system as recited in claim 15, further comprising a light source that includes the first color and the second color disposed to illuminate the operator's hands during the surgical procedure.

17. A non-transitory computer-readable medium carrying one or more sequences of instructions, wherein execution of the one or more sequences of instructions by one or more processors causes the one or more processors to perform the steps of:
capturing video data that views an operator's hands during a surgical procedure on a subject, wherein a dominant hand of the operator wears a first surgical glove having a first color on at least a portion of the first glove, and a non-dominant hand of the operator wears a second surgical glove having a different second color on at least a portion of the second glove;
for each of a plurality of frames of the video data, automatically determining, on a processor, a minimum rectangle of pixels, called a first rectangle, that encloses pixels having the first color;
determining automatically on a processor a first time series for a representative property of the first rectangle at the plurality of frames;
determining automatically on a processor a first value for a first measure of entropy based on the first time series; and
storing on a computer-readable medium a metric of operator performance based at least in part on the first value of the first measure of entropy.

* * * * *